United States Patent [19]

Born

[11] 4,324,146
[45] Apr. 13, 1982

[54] SAMPLING APPARATUS AND PROCESS

[75] Inventor: John W. Born, Brecksville, Ohio

[73] Assignee: The B. F. Goodrich Company, Akron, Ohio

[21] Appl. No.: 192,122

[22] Filed: Sep. 29, 1980

[51] Int. Cl.³ .......................................... G01N 31/06
[52] U.S. Cl. ............................. 73/863.12; 73/863.21; 422/88
[58] Field of Search .............. 73/1 G, 863.12, 863.21, 73/863.23; 422/88

[56] References Cited

U.S. PATENT DOCUMENTS 3,517,557  6/1970  Granger ........................... 73/863.12
3,614,855 10/1971  Vanluik ................................ 73/1 G
3,776,023 12/1973  Budd .................................... 73/1 G
3,888,112  6/1975  DeLecuu .............................. 73/1 G Primary Examiner—S. Clement Swisher
Attorney, Agent, or Firm—James R. Lindsay

[57] ABSTRACT

A sampling apparatus and process are provided for simultaneously collecting a sample of a pollutant from a measured quantity of ambient atmosphere and a sample of the pollutant from an equal quantity of the ambient atmosphere used in collecting the first sample plus a determined amount of the pollutant deliberately introduced into the second sample. The second sample is used to establish a compensation factor for correcting the determination of the amount of pollutant collected in the first sample for pollutant that passed through the sampling system without being entrapped.

6 Claims, 2 Drawing Figures

SAMPLING APPARATUS AND PROCESS

BACKGROUND OF THE INVENTION

The present invention pertains to apparatus and a process for simultaneously sampling the ambient atmosphere and for providing a calibration sample of the ambient atmosphere with a determinable amount of a pollutant normally present in the ambient atmosphere.

The measurement of trace amounts of pollutants in the ambient atmosphere has become of significant importance since there is some evidence that human exposure over a prolonged period of time to certain gases and volatiles that might be present in the ambient atmosphere may be detrimental to one's health. As a consequence of this finding, the government has imposed limitations on the amounts of certain materials that are permitted in the ambient atmosphere to which a person is subjected. Such limitations may provide for the presence of only a few "parts-per-million" of a particular pollutant measured over a specified period of time. The government requirements have made it necessary to at least periodically, if not essentially continuously, monitor the ambient atmosphere to make certain that pollutants that might be present in the ambient atmosphere at a particular location are maintained within "acceptable" levels.

A conventional analytical process for measuring the quantity of a pollutant in the ambient atmosphere over a specified period of time involves flowing ambient atmosphere at a known rate through a collector to be filled with activated charcoal particles for the prescribed period of time and absorbing the pollutant on the activated charcoal within the collector tube. The collector tube then is placed in a heater in which the collector tube is rapidly heated to cause the pollutant to be desorbed or "flashed" from the collector tube. The "flashed" pollutant sample is introduced into a gas chromatograph analyzer in which the quantity of the pollutant obtained from the collector tube is measured. The average concentration of the pollutant present in the ambient atmosphere during the measured time period is reported as "parts of pollutant per quantity of ambient temperature" (for example, "parts of pollutant per million parts of ambient atmosphere"). The accuracy of the test results depends primarily upon the efficiency of the collector tube in entrapping pollutant from the ambient atmosphere and in the effectiveness of releasing the pollutant from the collector tube during the "flashing" step.

It has been found that the humidity of the ambient atmosphere during the period of sampling significantly affects the accuracy of the test results. When sampling is done during a period in which the ambient atmosphere contains a high amount of moisture, some of the pollutant becomes desorbed by the moisture vapor and passes through the collector tube. Also, during a high humidity period the moisture vapor in the ambient atmosphere can occupy sites of the activated carbon within the collector tube that normally would "entrap" pollutant. The ability of the activated carbon to remove pollutant from the ambient atmosphere as a result is reduced and pollutant is permitted to pass through the collector tube without being entrapped on the activated carbon. The test results obtained, as a consequence, will indicate a lesser quantity of the pollutant in the ambient atmosphere than actually is present during the measured time interval.

SUMMARY OF THE INVENTION

The present invention provides sampling apparatus and a process for simultaneously collecting a sample of a pollutant from a measured quantity of ambient atmosphere and a sample of the pollutant from a measured quantity of the ambient atmosphere plus a determinable amount of the pollutant deliberately introduced into the sample. The accuracy of the test results then can be ascertained by comparing the reported quantity of pollutant in the samples and adjusting the test results to reflect the amount of pollutant that is determined to have passed through the collector tubes without being collected.

The invention will be more fully understood by reference to the following description of an embodiment of the invention when read in connection with the accompanying drawings.

DETAILED DESCRIPTION OF THE INVENTION

Figure 1:
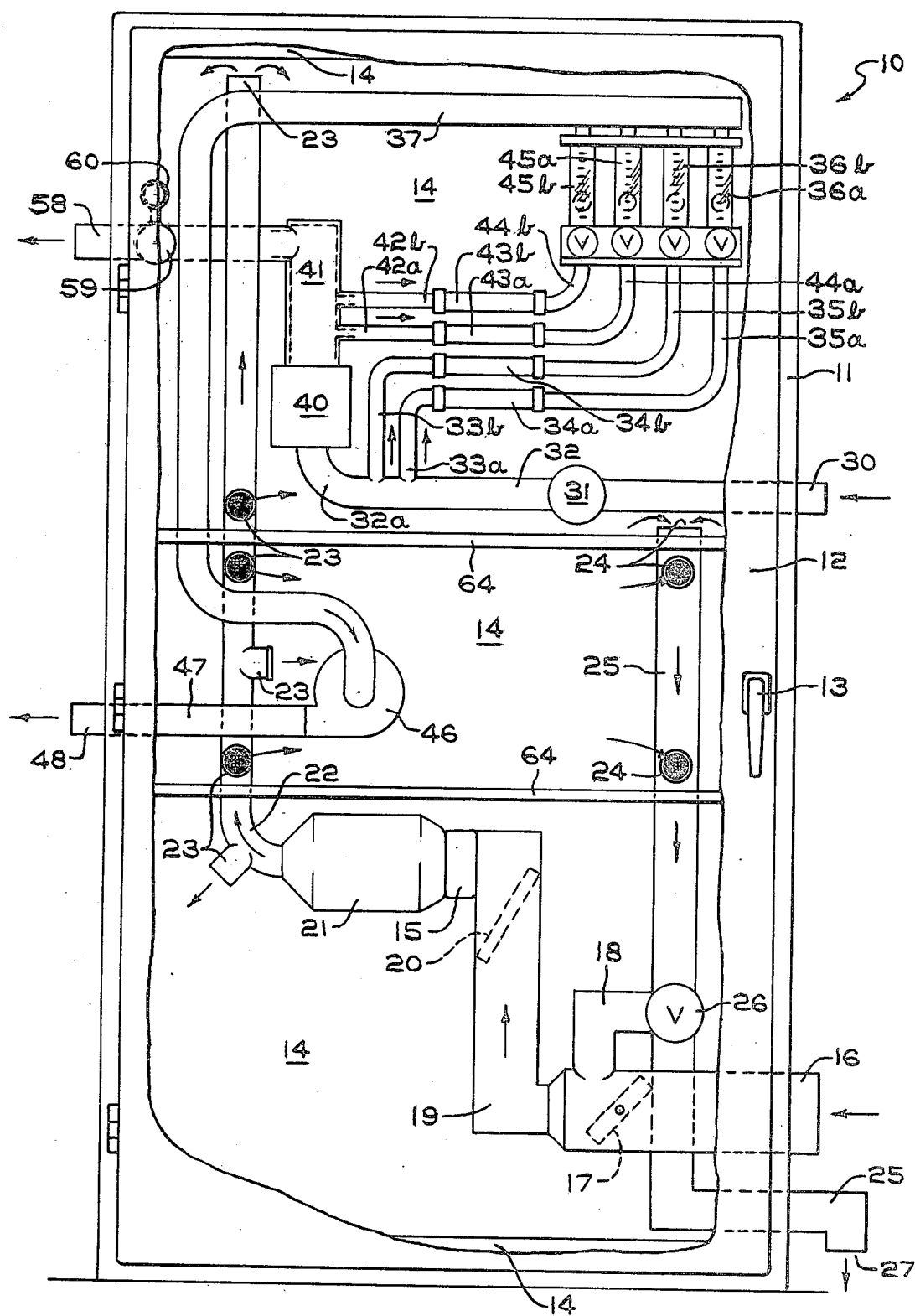
FIG. 1 is a schematic elevation view, partly broken away, of apparatus embodying the present invention.

Referring to the drawings, the sampling apparatus 10 comprises a cabinet 11 that includes a hinged door 12 capable of being secured in the "closed" position by latch 13. The interior of the cabinet 11 is lined with insulation 14 to permit the temperature within the cabinet 11 to be more easily maintained within a desired temperature range (preferably a temperature between about 25° and 40° C.) when the ambient temperature outside cabinet 11 is significantly above 40° C. or below 25° C. Air for regulating the temperature within cabinet 11 is circulated continually within the interior of cabinet 11 during the period of operation of the sampling apparatus 10 utilizing an air fan 15 positioned within an air circulation system such as hereinafter described.

As illustrated in FIG. 1, ambient air can be drawn into cabinet 11 from the outside atmosphere through air intake duct 16 which contains a regulator damper 17 for regulating the quantity of ambient atmospheric air drawn into cabinet 11 through intake duct 16. Air already within cabinet 11 also can be introduced into air intake duct 16 through duct 18 for recirculation within cabinet 11, as will be explained in greater detail hereinafter. The air egressing from air intake duct 16 flows into duct 19 and passes through a filter 20 which removes dust and other solid particles of significant size from the air. The air is drawn from duct 19 by fan 15 and flows into heater 21 which heats the air when necessary to maintain the air within cabinet 11 within the desired temperature range (for example, a temperature between 25° and 40° C.). Air discharged from heater 21 flows into duct 22 and is discharged into the interior of cabinet 11 through vents 23,23. Air is withdrawn from the interior of cabinet 11 through intake ports 24,24 and into duct 25. Valve 26 positioned at the juncture of duct 18 with duct 25 determines the quantity of air flowing in duct 25 that is diverted into duct 18 for recirculation and the quantity of air flowing in duct 25 that is discharged to the outside atmosphere through vent 27.

Valve 26 can be set to permit the entire volume of air drawn into duct 25 through intake ports 24,24 to be diverted into duct 18 or the entire volume of air drawn into duct 25 to be discharged through vent 27, as well as proportioning the amount of air to be diverted to duct 18 and to be discharged to the ambient atmosphere. Heater 21 is thermostatically controlled to provide heating whenever the temperature of the air circulating within the interior of cabinet 11 falls below a desired temperature within the temperature range at which the interior of cabinet 11 is to be maintained. The air circulating system described above does not provide the ambient air from which the test samples or calibration samples are obtained, but only serves as a means for maintaining the interior of cabinet 11 at a temperature within the desired temperature range.

The test samples and calibration samples used for determining the amount of a pollutant (for example, vinyl chloride monomer) in the ambient atmosphere are prepared using ambient air which is drawn into cabinet 11 through intake duct 30. Air entering intake duct 30 then travels through a filter unit 31 (for example, a "cyclone filter") which removes particles of dust and other solid particulate material from the air. The filtered air leaves filter unit 31 and enters manifold 32 which is provided with lateral pipes 33a, 33b through which ambient air is drawn at a controlled rate. The ambient air streams flowing from lateral pipes 33a, 33b are drawn through collector tubes 34a, 34b which remove pollutant from the respective air streams as they flow through the collector tubes 34a, 34b. The two air streams emitted from collector tubes 34a, 34b flow through tubes 35a, 35b and through flow meters 36a, 36b and into duct 37. Each of the flow meters 36a, 36b is provided with a valve for regulating the volume rate of air flowing from lateral pipes 33a, 33b and through collector tubes 34a, 34b.

The remaining portion of the air flow into manifold 32 that is not diverted into lateral pipes 33a, 33b is discharged from manifold 32 and flows through permeation chamber 40 and into manifold 41 provided with lateral pipes 42a, 42b through which air discharged from permeation chamber 40 is drawn at a controlled rate. The air streams flowing from lateral pipes 42a, 42b are drawn through collector tubes 43a, 43b, flow through tubes 44a, 44b and flow meters 45a, 45b and then into duct 37. Pump 46 connected to duct 37 creates the suction force to draw the air streams from manifold 32 through lateral pipes 33a, 33b and from manifold 41 through lateral pipes 42a, 42b and ultimately into duct 37. The air expelled from pump 46 flows into duct 47 and is discharged through discharge vent 48 to the atmosphere surrounding cabinet 11.

Figure 2:
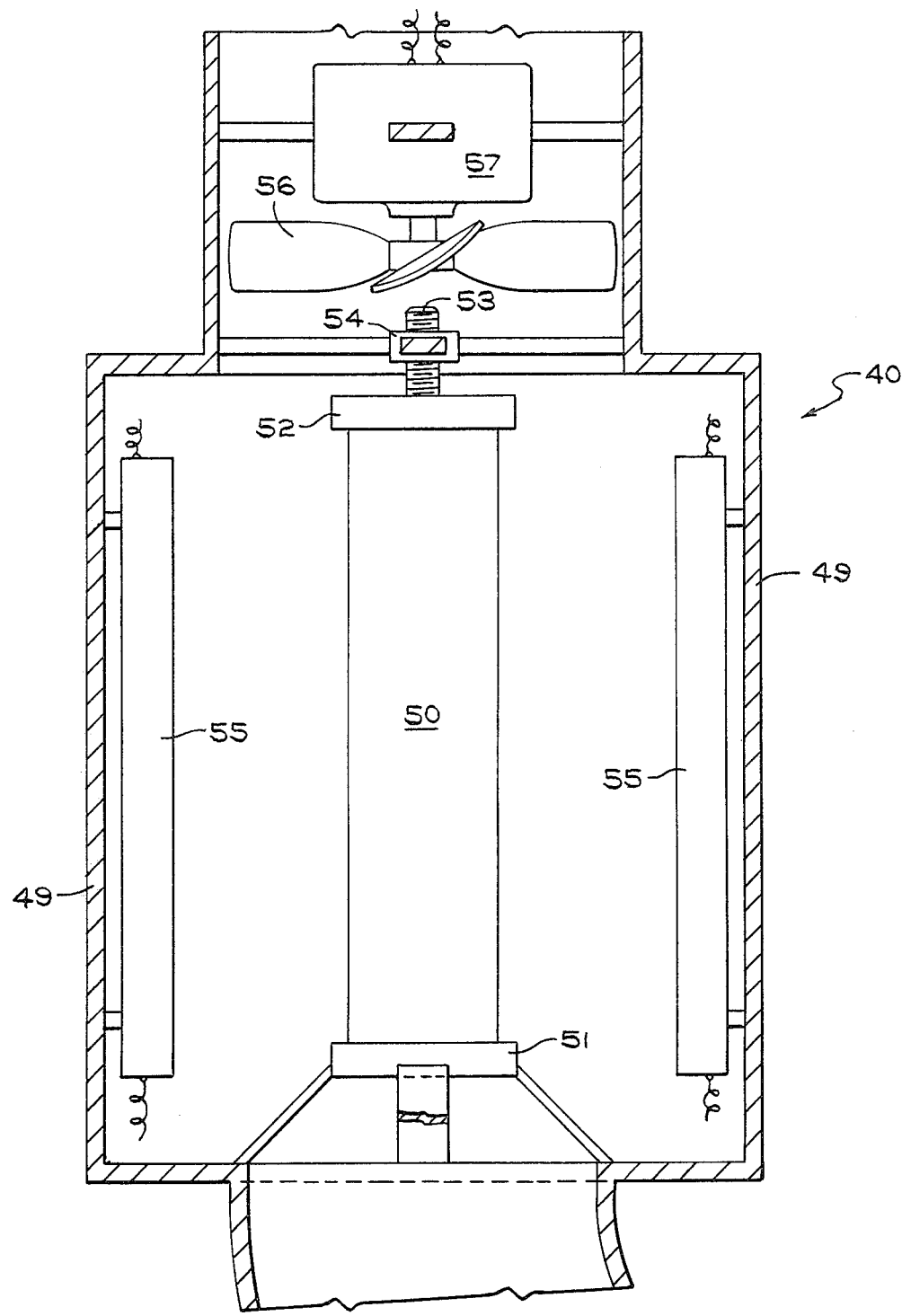
FIG. 2 is an elevation view, partly broken away and in section, of the permeation chamber shown in FIG. 1.

As shown in FIG. 2, permeation chamber 40 is comprised of a housing 49 that contains a permeation tube 50 that contains a quantity of the same pollutant in the ambient atmosphere for which quantity determinations are being made. The permeation tube 50 is constructed to allow the pollutant contained in the tube 50 to slowly diffuse from the tube 50 into housing 49 and be mixed with the air flowing through permeation chamber 50. Such tubes are well known and can be obtained from several sources. For example, permeation tubes which may be used in apparatus 10 can be obtained from Analytical Instrument Development, Inc., located in Avondale, Pennsylvania. Permeation tube 50 is retained within housing 49 between fixed support 51 and support 52 which is provided with a threaded stud 53 fitted through a fixed nut 54 to permit support 52 to be moved away from permeation tube 50 a sufficient distance so that permeation tube 50 can be lifted out of support 51 and removed from housing 49 though an access door (not shown) in housing 49. Thermostatically-controlled heaters 55,55 contained within housing 49 maintain the temperature within permeation chamber 40 within a desired temperature range within which pollutant is discharged from permeation tube 50 at a desired rate. A suction fan 56 contained within housing 49 and driven by motor 57 creates a suction that draws ambient air into intake duct 30, through filter 31, through manifold 32 and through permeation chamber 40 discharges the air from permeation chamber 40 into manifold 41 and causes air introduced into manifold 41 that is not drawn into lateral pipes 42a, 42b to flow through duct 58 and be vented into the atmosphere outside cabinet 11. A valve 59 located within duct 58 is fitted with a flow gage 60 and provides a control for regulating the volume of air drawn into intake duct 30. If desired, an absorption filter (not shown) can be fitted within duct 58 to remove any pollutant from the air before it is vented to the atmosphere.

If desired, cabinet 11 can be divided into more than one compartment by partitions or separators 64,64 which provide supporting surfaces on which various components housed within cabinet 11 can be conveniently mounted.

In utilizing apparatus 10 for sampling the ambient atmosphere and for simultaneously providing a calibration sample of ambient atmosphere and a determinable amount of a pollutant for which a concentration determination is to be made, a permeation tube 50 is selected that contains the same chemical material for which a pollutant determination is to be made. For example, if a determination of the quantity of vinyl chloride monomer pollutant present in the ambient atmosphere over a selected period of time is to be made, a permeation tube 50 containing vinyl chloride monomer is selected for use in permeation chamber 40 of sampling apparatus 10. As indicated above, permeation tubes containing various chemical materials can be obtained from a variety of known sources. Such permeation tubes are constructed to emit the contained chemical material at essentially a uniform rate within a restricted temperature range during the operating life of the tube. Before inserting the permeation tube 50 into permeation chamber 40, the temperature within cabinet 11 is brought within the desired temperature range by circulating air (by means of fan 15) through heater 21 and into the interior of cabinet 11, regulating the proportion of air being drawn from the ambient atmosphere and being recirculated within cabinet 11 through use of damper 17 and valve 26 so as to maintain the temperature within cabinet 11 within the desired temperature range. Clean collector tubes 33a, 33b, 43a and 43b are inserted in their respective positions within the sampling lines of cabinet 11 (as is illustrated in FIG. 1). The permeation tube 50 then is weighed (desirably, at least to the nearest 1/10,000th gram) and is secured in place within permeation chamber 40. Suction fan 56 of permeation chamber 40 is activated by energizing motor 57 to cause a flow of ambient air to be drawn into intake duct 30, through manifold 32 and permeation chamber 40 and through manifold 41. Contemporaneously, centrifugal pump 46 is activated to create a suction to draw air streams into the lateral pipes 33a and 33b of manifold 32 and through collector tubes 34a and 34b respectively and to draw air streams into the laterial pipes 42a and 42b of manifold 41 and through collector tubes 43a and 43b respectively. The volume of each air stream drawn through collector tubes 34a, 34b, 43a and 43b is regulated by adjustment of the needle valves associated with flow meters 36a, 36b, 45a and 45b, the valves being regulated so that the rate of flow of each air stream that passes through collector tubes 34a, 34b, 43a and 43b is the same (for example, a rate of 10 milliliters per minute for each air stream). The volume of air flowing from manifold 41 into duct 58 and discharged to the atmosphere is regulated by valve 59 positioned in duct 58. It will be appreciated that the total volume of ambient air drawn into cabinet 11 through intake duct 30 (desirably, about 5 liters of air per minute) is regulated by the settings of the needle valves of flow meters 36a, 36b, 45a and 45b and the setting of valve 59. It will be further appreciated that the volume of air flowing through permeation chamber 40 over a designated period of time is the summation of the volumes of air flowing through flow meters 45a and 45b and through duct 58 during the designated time period. At the start of the sampling operation, heaters 55,55 in permeation chamber 40 are energized to maintain the temperature within permeation chamber 40 at a desired temperature for proper functioning of permeation tube 50 (generally, 35° to 40° C.).

After cabinet air has flowed through the sampling system over the period of time sampling is to occur (for example, an eight hour period), pump 46 and suction fan 56 are shut off to stop the intake of ambient air into intake duct 30. Permeation tube 50 is removed from permeation chamber 40 and again is weighed (desirably to the nearest 1/10,000 gram). The loss in weight of permeation tube 50 occurring between the time sampling commenced and the time sampling ended represents the weight of the chemical material within permeation tube 50 that was released from permeation tube 50 into the air flowing through permeation chamber 40 during the sampling time period.

Collector tubes 34a, 34b, 43a and 43b then are removed and transferred to conventional "flasher" or desorber heater units used in connection with gas chromatograph analyzers. Each collector tube (34a, 34b, 43a and 43b) is "flashed" individually to cause the volatiles entrapped by the activated charcoal within the collector tube to become desorbed and freed from the activated charcoal. The desorbed volatiles from each collector tube 34a, 34b, 43a and 43b then is introduced as a separate sample into a gas chromatograph analyzer for determination of the quantity of various volatiles contained in the sample.

It will be understood that the volatiles contained in the samples obtained from collector tubes 34a and 34b are volatiles entrapped only from ambient air drawn from the atmosphere adjacent to cabinet 11, and that the volatiles contained in the samples obtained from collector tubes 43a and 43b are volatiles entrapped not only from ambient air drawn from the atmosphere but include also a portion of chemical substance emitted from permeator tube 50 into the air flowing through permeator chamber 40 during the sampling time period. Since the volume of air drawn through each collector tube 43a and 43b during the sampling time period can be determined using the rate of flow per unit of time through flow meters 45a and 45b and since the volume of air discharged through duct 58 during the sampling time period can be determined using the rate of flow per unit of time through valve 59 as determined by flow gage 60, the amount of chemical material emitted by permeation tube 50 during the sampling time period that was absorbed by each collector tube 43a and 43b and that was discharged from manifold 41 into exhaust duct 58 can readily be determined by volume proportioning of the various air flows. From the gas chromatograph analyses obtained from the desorbed samples obtained from collector tubes 34a, 34b, 43a and 43b, a compensation factor can be derived for use in correcting the pollutant content values determined by the analyses of the desorbed samples obtained from collector tubes 34a and 34b to provide for pollutant that passed through collector tubes 34a and 34b without being entrapped.

The compensation factor (K) can be derived by subtracting the weight of permeation tube 50 immediately following the completion of the sampling time period from the weight of permeation tube 50 immediately before the start of the sampling time period to ascertain the weight of the chemical material emitted by permeation tube 50 during the sampling time period (Wp). The total volume of air that flows through permeation chamber 40 during the sampling time period ($V_T$) is determined by adding the volume of flow through collector tube 43a ($V_1$), collector tube 43b ($V_2$) and through exhaust duct 58 ($V_3$). The concentration of chemical material in the air that flowed through permeation chamber 40 during the sampling time period resulting from the introduction of chemical material from permeation tube 50 during such period (Cp) can be determined by dividing Wp by $V_T$. The weight of the chemical material emitted from permeation tube 50 that flowed into collector tube 43a ($W_1$) during the sampling time period would be:

$$W_1 = W_p \times [V_1/(V_1 + V_2 + V_3).]$$

Also, the weight of the chemical material emitted from permeation tube 50 that flowed into collector tube 43b ($W_2$) during the sampling time period would be:

$$W_2 = W_p \times [V_2/(V_1 + V_2 + V_3).]$$

Since the volume of flow through collector tube 43a and through collector tube 43b are equal, then $W_1$ will equal $W_2$ (within experimental error). $W_1$ and $W_2$ can be converted to a concentration of the chemical material per volume unit (for example, milligrams of the chemical material per cubic meter of air) by dividing $W_1$ by $V_1$ to give a concentration $C_{c1}$, and $W_2$ by $V_2$ to give a concentration $C_{c2}$ (converted, of course, to the desired units of measure). The amounts of the chemical material (present as a pollutant) in the samples obtained from collector tubes 34a and 34b and determined by gas chromatograph analysis are determined and expressed as a concentration ($C_{f1}$ and $C_{f2}$). Again, since the volumes of air flow during the sampling time period that flowed through collector tubes 34a and 34b are equal, $C_{f1}$ and $C_{f2}$ would be the same (within experimental error). From the data, the compensation factor (K) is determined from the following calculation:

$$K = C_p/(C_{c1} - C_{f1})$$

The concentrations of the pollutant in the ambient atmosphere determined by analysis of the samples collected from collector tubes 34a and 34b are multiplied by the compensation factor (K) to correct the determinations for loss of pollutant through collector tubes 34a and 34b.

Collector tubes 34a, 34b, 43a and 43b can be any of the commercial collector tubes designed for entrapping volatile materials contained in a gaseous sample flowed through the tube (for example, "Bendix Flasher Tubes" manufactured by The Bendix Corporation).

A commercial permeation chamber which can be used in the sampling apparatus is the Model 340 Portable Calibrator chamber manufactured by Analytical Instrument Development, Inc. In addition to heaters, a suction fan and provision for securing a permeation tube within its interior, the chamber also contains a flow meter for measuring and regulating the volume of air drawn through the chamber, thereby eliminating the need for valve 59 and flow gage 60 in duct 58 of the apparatus shown in the drawings.

While the embodiment of this invention described illustrates collection of two samples from manifold 32 and two samples from manifold 41, it will be appreciated that a single sample or more than two samples can be collected from each manifold without departing from the present invention.

It will be understood that the above-described embodiment of this invention is susceptible to various other modifications, changes and adaptations and that the same are intended to be comprehended within the meaning of the appended claims.

I claim:

1. Sampling apparatus for collecting a sample of pollutant obtained from a determinable quantity of ambient atmosphere and for simultaneously collecting a second sample of the same pollutant obtained from an essentially equal quantity of ambient atmosphere plus a determinable quantity of the same pollutant deliberately introduced into said second sample, said apparatus comprising:
   a. a cabinet provided with means for access into the interior thereof,
   b. means for controlling the temperature within said cabinet,
   c. means for drawing ambient atmosphere during a sampling period from outside said cabinet continuously into a sampling system housed within said cabinet,
   d. said means for drawing ambient atmosphere from outside said cabinet into said sampling system including means for continuously diverting a portion of said ambient atmosphere at a controlled rate into and through a first collector device provided with means for releasably entrapping a pollutant contained in the portion of ambient atmosphere travelling therethrough,
   e. said means for drawing ambient atmosphere from outside said cabinet into said sampling system including means for continuously drawing a second portion of said ambient atmosphere at a controlled rate through a permeation chamber adapted to release said pollutant contained in the ambient atmosphere into said second portion of said ambient atmosphere at essentially a constant rate as said second portion of said ambient atmosphere travels through said permeation chamber,
   f. said means for drawing ambient atmosphere from outside said cabinet into said sampling system including means for continuously diverting at a controlled rate a portion of the discharge from said permeation chamber into and through a second collector device provided with means for releasably entrapping herein said pollutant contained in the diverted sample, said rate at which said portion is diverted through said second collector device being essentially equal to the rate of flow of ambient atmosphere being drawn through said first collector tube, and
   g. means for determining the quantity of ambient atmosphere drawn into said sampling system during the sampling period and for determining the quantities of flow through said first collector device and said second collector device.

2. The sampling apparatus of claim 1 wherein said means for drawing ambient atmosphere during a sampling period from outside said cabinet continuously into a sampling system housed within said cabinet includes means for removing solid particulate materials from said ambient atmosphere before any of said ambient atmosphere flows into either of said collector tubes.

3. The sampling apparatus of claim 1 wherein said means for controlling the temperature within said cabinet includes means for circulating air within the interior of said cabinet and heating means for heating the circulating air if the temperature of the circulating air falls below a desired temperature.

4. The sampling apparatus of claim 1 wherein said means for controlling the temperature within said cabinet includes means for drawing air into the cabinet from outside of said cabinet and means for regulating the proportion of circulating air drawn from the outside of said cabinet and recirculated from within the said cabinet.

5. The sampling apparatus of claim 1 wherein said permeation chamber includes heating means for maintaining the interior of said permeation chamber at a desired temperature.

6. A process for collecting a sample of pollutant from a determinable quantity of ambient atmosphere and for simultaneously collecting a second sample of pollutant from an essentially equal quantity of ambient atmosphere plus a determinable quantity of the same pollutant which comprises:
   a. flowing ambient atmosphere during a sampling time period at a known flow rate through a first collector device capable of releasably entrapping therein pollutant contained in said ambient atmosphere,
   b. flowing ambient atmosphere during said sampling time period through a permeation chamber and introducing a determinable quantity of said pollutant into said ambient atmosphere flowing through said permeation chamber,
   c. flowing a portion of the discharge flow from said permeation chamber during the said sampling time period at a rate essentially equal to the flow rate at which ambient atmosphere is travelling through the aforesaid first collector device through a second collector device capable of releasably entrapping therein said pollutant contained in the said discharge flow from said permeation chamber, and
   d. discontinuing the air flows through the said first collector device and second collector device at the end of the sampling time period.

* * * * *